(12) United States Patent
Wallace

(10) Patent No.: US 6,209,541 B1
(45) Date of Patent: *Apr. 3, 2001

(54) HYDROPHOBIC ELECTROSTATIC BREATHING FILTERS, AND METHODS OF MANUFACTURING THE SAME

(75) Inventor: Dean Wallace, Fort Myers, FL (US)

(73) Assignee: SIMS Portex Inc., Keene, NH (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/030,398

(22) Filed: Feb. 25, 1998

(51) Int. Cl.⁷ .................................................. A62B 23/02
(52) U.S. Cl. ............................. 128/205.27; 128/200.24; 128/205.12; 128/205.29; 210/445; 55/511
(58) Field of Search .................... 128/205.27, 205.12, 128/201.13, 200.24, 205.29, 912, DIG. 26, 204.18, 206.12; 95/90, 196; 96/154, 132, 77; 55/474, 491, 510, 511

(56) References Cited

U.S. PATENT DOCUMENTS

| | | | |
|---|---|---|---|
| 3,782,083 | * 1/1974 | Rosenberg | 128/205.12 |
| 3,803,810 | * 4/1974 | Rosenberg | 128/205.12 |
| 3,932,153 | * 1/1976 | Byrns | 55/511 |
| 4,229,306 | 10/1980 | Hein et al. | 210/446 |
| 4,386,948 | 6/1983 | Choksi et al. | 55/499 |
| 4,404,006 | 9/1983 | Williams et al. | 55/502 |
| 4,414,172 | 11/1983 | Leason | 264/355 |
| 4,444,661 | 4/1984 | Jackson et al. | 210/446 |
| 4,479,874 | 10/1984 | Rosenberg et al. | 210/445 |
| 4,529,419 | 7/1985 | Perl et al. | 55/158 |
| 4,874,513 | 10/1989 | Chakraborty et al. | 210/321.84 |
| 4,900,411 | 2/1990 | Graus et al. | 210/321.84 |
| 5,011,555 | * 4/1991 | Sager | 55/511 |
| 5,033,507 | 7/1991 | Pouchot | 128/206.17 |
| 5,035,236 | 7/1991 | Kanegaonkar | 128/201.13 |
| 5,038,775 | 8/1991 | Maruscak et al. | 128/205.27 |
| 5,052,385 | 10/1991 | Sundstrom | 128/205.27 |
| 5,158,077 | * 10/1992 | Sundstrom | 128/205.27 |
| 5,195,527 | * 3/1993 | Hicks | 128/205.12 |
| 5,213,096 | * 5/1993 | Kihlberg et al. | 128/205.12 |
| 5,230,727 | * 7/1993 | Pound et al. | 55/511 |
| 5,269,917 | 12/1993 | Stankowski | 210/232 |
| 5,320,096 | 6/1994 | Hans | 128/205.29 |
| 5,337,739 | * 8/1994 | Lehman | 128/205.27 |
| 5,443,723 | 8/1995 | Stankowski et al. | 210/321.75 |
| 5,478,377 | 12/1995 | Scavnicky et al. | 96/17 |
| 5,540,756 | 7/1996 | Hoppitt et al. | 95/69 |
| 5,545,242 | 8/1996 | Whitlock et al. | 55/502 |
| 5,556,541 | 9/1996 | Ruschke | 510/232 |
| 5,590,644 | 1/1997 | Rosenkoetter | 128/201.13 |

(List continued on next page.)

Primary Examiner—John G. Weiss
Assistant Examiner—V. Srivastava
(74) Attorney, Agent, or Firm—Connolly Bove Lodge & Hutz

(57) ABSTRACT

A hydrophobic electrostatic breathing filter is fabricated by applying a thin layer of adhesive to the pinch ring of a patient side filter housing portion. A hydrophobic membrane is positioned over the adhesively coated pinch ring to effect a hermetic seal between the pinch ring and membrane using the adhesive interface. Electrostatic filter media and scrim are positioned adjacent the pinch ring of a machine side filter housing portion, and the patient and machine side portions of the housing are then welded together to hold the electrostatic filter media/scrim in place adjacent the hermetically sealed hydrophobic membrane by a mechanical clamping force exerted by the pinch rings. The resultant filter includes a hydrophobic membrane which is hermetically sealed across the patient side of the filter housing, and an electrostatic filter media/scrim element which is independent of the hydrophobic membrane and which is mechanically held in place adjacent the hydrophobic membrane.

15 Claims, 1 Drawing Sheet

U.S. PATENT DOCUMENTS 5,671,754 * 9/1997 Schmukler et al. .................. 128/844
5,674,481 * 10/1997 Wahi .............................. 128/205.27
5,706,804 * 1/1998 Baumann et al. .............. 128/206.19
5,723,047 * 3/1998 Turnbull ................................. 55/511
5,732,695 * 3/1998 Metzger ........................... 128/206.12
5,829,428 * 11/1998 Walters et al. .................. 128/204.18

* cited by examiner

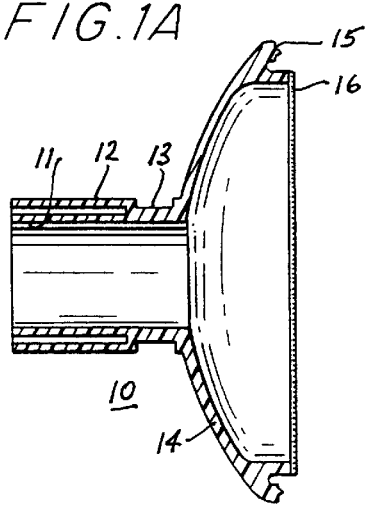
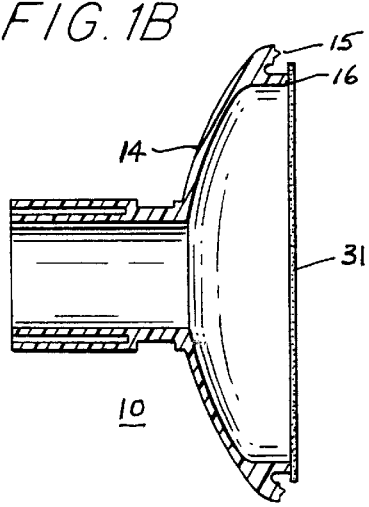
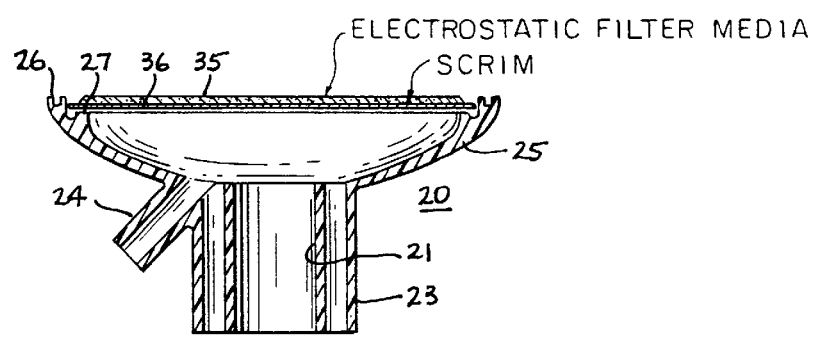
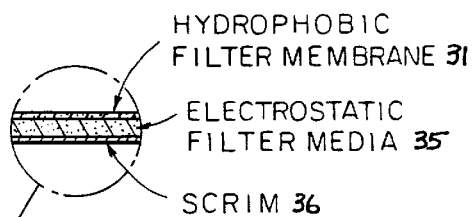
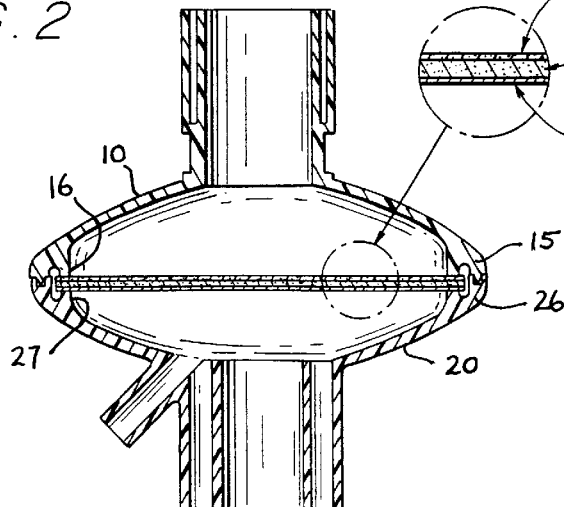

HYDROPHOBIC ELECTROSTATIC BREATHING FILTERS, AND METHODS OF MANUFACTURING THE SAME

BACKGROUND OF THE INVENTION

The present invention relates to medical-surgical breathing filters, and is more particularly concerned with breathing filters that include electrostatic filter media.

Electrostatic breathing filters have been used since the early 1980s to filter breathing gases. The filter media consists of polypropylene fibers which have been made electrostatic by a corona discharge process. The fibers are needled so that they intertwine, thus forming a relatively flat filter pack which electrostatically captures particulate from gases moving through the filter's open passageways. Electrostatic filters are effective as bacteria and viral filters in medical device breathing filters, but are not considered to be HEPA filters. Their use can nevertheless be justified by their filtration effectiveness as well as by their relatively low cost. Electrostatic filter packs do not need to be hermetically sealed around their periphery as particulate is attracted and attaches to the surfaces of the fibers. It is only necessary that the construction of a filter housing containing an electrostatic filter pack includes internal means, such as peripheral annular baffles, to direct the flow of gas towards and over the surface of the filter media.

Electrostatic filters are not effective in filtration of liquids as liquids tend to quickly discharge the electrostatic fibers. Liquids can also easily penetrate through the filter's open passageways. Therefore, when used in a breathing filter, an electrostatic filter pack should be shielded from contact with body fluids such as mucosal secretions since these fluids tend to neutralize the electrostatic charge, making filtration less efficient. Further, body fluids could pass through the filter media, exposing other parts of the breathing systems to possible contamination. Hydrophobic (water repellant) membranes are known and have been used to prevent passage of fluids. More particularly, electrostatic breathing filters have been fabricated with a combination of a hydrophobic membrane, electrostatic filter media, scrim (a nonwoven polypropylene mesh) and, in some cases, another hydrophobic membrane. This combination has been used to protect the media body from fluids that would otherwise tend to enter it from either direction.

Filter packs of the aforementioned type, i.e., using one or two hydrophobic membranes, filter media, and scrim are fabricated with the outside periphery of the pack heat-sealed in a manner that causes the pack to become one single unit. Such a single unit filter pack is then placed within two halves of a filter housing, and the housing is welded or glued to enclose the filter pack therein. Pinch rings have sometimes been provided near the periphery of the filter housing to hold the single unit filter pack in place and to prevent bypass of fluid around the outside periphery of the filter pack. This arrangement, however, because of plastic and filter pack dimensional tolerance stack up, does not assure that fluid will not flow between the pinch rings and filter pack.

An alternate method of obtaining a fluid seal has been to encapsulate the periphery of the single unit filter pack with a flexible sealant such as silicone, and to then depend upon pinch rings in the housing to compress against the flexible sealant. This approach increases the expense of the manufacturing process and, as in the previously described method of fabrication, fails to assure the presence of a hermetic seal that prevents passage of fluid through the device.

The present invention is intended to provide a method of manufacture which is less expensive than methods suggested heretofore, and which results in the production of a hydrophobic electrostatic breathing filter that eliminates the foregoing problems.

BRIEF SUMMARY OF THE INVENTION

A hydrophobic electrostatic filter constructed in accordance with the present invention comprises a housing having a patient side portion and a machine side portion. Each of these housing portions includes an outer annular edge and an annular pinch ring inward of the outer edge. The filter is fabricated by applying a thin layer of an adhesive to the pinch ring of the patient side housing portion, and then positioning a hydrophobic membrane over that pinch ring to effect a hermetic seal between the hydrophobic membrane and the patient side housing portion utilizing an adhesive interface. Electrostatic filter media and scrim are positioned within the machine side portion of the housing adjacent the pinch ring of said machine the portion, the two housing portions are then engaged in opposing relation to one another to position the pinch rings of the housing portions in at least partially opposed relation to one another, and the outer edges of the engaged housing portions are sealed together by a hot melt adhesive or by ultrasonic welding to form an enclosed filter housing that includes the electrostatic filter media and scrim mechanically fixed in place between the opposed parts of the pinch rings adjacent to the hermetically sealed hydrophobic membrane.

The foregoing method of assembly results in a breathing filter which consists of a hydrophobic membrane that is separate from and independent of the electrostatic media, but which nevertheless protects the electrostatic filter media from exposure to liquids. Particulate migration of electrostatic fibers at the machine side of the housing is prevented by scrim that is located immediately adjacent the electrostatic media element on the side of the media facing the machine side portion of the housing.

The method of assembly simplifies the entire manufacturing process since it is relatively easy to seal the hydrophobic membrane to the pinch ring on the patient side of the housing, and since, further, the electrostatic media does not need to be part of the hermetic seal. The assembly method also provides a high degree of assurance that the hydrophobic membrane will retain its integrity before and after the assembly process.

BRIEF DESCRIPTION OF THE DRAWINGS

The foregoing aspects of the present invention will be more particularly described by reference to the accompanying drawings in which:

FIG. 1A depicts the patient side portion of a breathing filter constructed in accordance with the present invention, and a first step in the method of manufacturing the filter;

FIG. 1B depicts the structure shown in FIG. 1A, and a second step in the method of manufacture;

FIG. 1C depicts the machine side portion of the breathing filter, and a third step in the method of manufacture;

FIG. 2 depicts an assembled breathing filter constructed in accordance with the present invention, and a fourth step in the method of manufacture; and FIG. 2A is an enlarged view of a portion of the filter pack shown in FIG. 2.

DETAILED DESCRIPTION OF THE EMBODIMENTS

The patient side housing portion of a breathing filter constructed in accordance with the present invention is depicted in FIGS. 1A and 1B. The patient side housing portion, generally designated 10, is fabricated of plastic material, i.e., injection molded K-resin (styrene-butadiene), includes a 15 mm female conical connector 11, a 22 mm male conical connector 12 having an anti-disconnect recess 13, and a bell shaped portion 14 having an annular outer edge 15 and an annular pinch ring 16 located inward of and coaxial with outer edge 15. A logo of a man (not shown) is provided on an outer surface of housing portion 10 to indicate the patient end of an assembled breathing filter.

The machine side portion of the filter, designated 20, is shown in FIG. 1C. It is fabricated of the same material as the patient side portion of the housing, includes a 15 mm male conical connector 21, a 22 mm female connector 23, Luer Lock gas sampling port connectors one of which is designated 24, a bell shaped portion 25 that includes an outer edge 26 which is congruent with outer edge 15 of the patient side portion of the housing, and an annular pinch ring 27 disposed inward of and coaxial with outer edge 26.

In a first step of the manufacturing process, the patient side portion of the housing is placed in an assembly fixture, and a thin film (e.g., having a thickness of 0.015 inches) of hot melt adhesive 30 is applied to the entire outer surface of pinch ring 16 (see FIG. 1A).

In the next step of fabrication shown in FIG. 1B, the outside peripheral flat surface of a hydrophobic membrane 31 is placed on the adhesively coated flat surface of the pinch ring 16 and bonded to pinch ring 16 to hermetically seal the patient side portion of the housing using an adhesive interface. By employing appropriate assembly fixtures, the location of the hydrophobic element 31 relative to pinch ring 16 remains consistent and repeatable. Assembly fixtures are also used to assure a consistent, repeatable application of the hot melt adhesive, or any other adhesive system that is employed, to the flat surface of the pinch ring 16 prior to fixation of the hydrophobic membrane 31 onto the pinch ring. Using such assembly fixtures, the housing side portion 10 having the adhesively coated pinch ring is pressed against hydrophobic membrane 31 which is precisely located with respect to the pinch ring 16. The adhesive bond takes place almost immediately, i.e., in less than 2 seconds. This assures a repeatable, accurately located hermetic seal between hydrophobic membrane 31 and the patient side portion 10 of the housing.

The hydrophobic membrane is 0.010 inches thick, and is a commercially available non-woven polypropylene. It has a weight of 1.4 oz/sq. yd., an air permeability of 70 CFM, and a hydrostatic head of 54 cm $H_2O$.

The hot melt adhesive 30 used to glue the hydrophobic membrane 31 to the patient side 10 of the filter housing is also commercially available, has a softening point of 175° F., is applied at a temperature of 350° F., and has a viscosity at 300° F. of 100 centipoise.

In a third step of the method of manufacture, shown in FIG. 1C, electrostatic filter media 35 (and scrim 36, if utilized) is placed in a recessed portion of the machine side filter housing portion 20, again utilizing an appropriate assembly fixture, for support on the pinch ring 27 of the machine side housing portion. The electrostatic filter media 35 is electrostatically charged polypropylene, which is commercially available in weights of 50 grams per square meter to 300 grams per square meter. The electrostatic media used in the present invention is preferably of 200 gram weight to limit the pressure drop so that it cannot exceed 2.5 cm $H_2O$ @ 60 l/min.flow. Scrim 36 is a non-woven web of polypropylene fibers, and is preferably located below electrostatic media 35, i.e., between media 35 and the interior of machine side housing portion 20, to prevent particulate migration of electrostatic fibers at the machine side of the housing enclosure. The outer edge of scrim 36 may be bonded, e.g., heat sealed, to the outer edge of electrostatic filter media 35.

The final step of the assembly procedure is shown in FIG. 2, i.e., the completed patient side portion of the filter shown in FIG. 1B is placed on the assembled elements of the machine side portion of the filter shown in FIG. 1C, so that the outer edges 15 and 26 of housing portions 10 and 20 abut one another (or interengage one another when these outer edges are configured in the manner shown in FIGS. 1A and 1C), and the outer edges of the patient and machine sides of the housing enclosure are then hermetically sealed together utilizing an adhesive, or ultrasonic welding. When the housing sides are positioned to abut one another, the pinch rings 16 and 27 are disposed in at least partially opposing relation to one another, and are preferably in directly opposing relation to one another, so as to exert a mechanical clamping force which holds elements 35, 36 in place adjacent hydrophobic membrane 31. The pinch rings are sized to fix the electrostatic filter media and scrim in their desired position within the completed filter enclosure, adjacent membrane 31, solely as a result of the aforementioned clamping force. A liquid tight seal is not required since a hermetic seal has already been obtained by the assembly steps shown in FIGS. 1A and 1B.

Positioning and fixation of the hydrophobic membrane 31 is a critical part of the assembly procedure, since it assures that a hermetic seal is effected across the patient side portion of the housing, prior to subsequent assembly operations. The remainder of the assembly operations, i.e., placement of the electrostatic filter media within the housing enclosure and the adhesive or ultrasonic closure of the complete housing, can be accomplished using established assembly techniques without the need to encapsulate or seal the electrostatic media since the electrostatic media is protected from exposure to liquids by the hydrophobic characteristics of independent membrane 31.

The filter pack resulting from the foregoing assembly steps is shown in greater detail in FIG. 2a and consists of two independent elements, i.e., the hydrophobic membrane 31, and the two part filter pack 35, 36 which is independent of hydrophobic membrane 31. The significant advantages achieved by a hydrophobic electrostatic breathing filter so configured, and by the assembly technique described above used to produce such a breathing filter, have been described previously.

Having thus described my invention, I claim:

1. A hydrophobic electrostatic breathing filter comprising a housing having a patient side portion and a machine side portion, a hydrophobic membrane extending across the interior of said patient side portion, said membrane having an outer periphery, and an electrostatic filter element extending across said machine side portion of said housing adjacent a side of said hydrophobic membrane that faces said machine side portion, said electrostatic filter element being independent of said hydrophobic membrane wherein said hydrophobic membrane and said electrostatic filter element are retained with the housing in different manners, said hydrophobic membrane being retained first by a sealing bond around said outer periphery of said membrane between said membrane and the interior of said housing to isolate said patient side portion of said housing from said machine side portion of said housing, and said electrostatic filter subsequently being held in place adjacent said hydrophobic membrane solely by a mechanical clamp force exerted on said electrostatic filter element by an interior portion of said housing so that said patient side portion of said housing is isolated from said machine side portion by said hydrophobic membrane during assembly of said electrostatic filter.

2. The filter of claim 1 wherein said hydrophobic membrane is sealed to interior of said housing by an adhesive interface.

3. A hydrophobic electrostatic breathing filter comprising a patient side filter housing portion and a machine side filter housing portion, each of said housing portions including an annular outer edge and an annular pinch ring coaxial with and inward of said outer edge, said outer edges of said housing portions being congruent and sealed together to form an enclosed filter housing, said pinch rings of said housing portions being disposed respectively in opposing relation to one another within said enclosed housing, a hydrophobic membrane an electrostatic filter element that is independent of said hydrophobic membrane and which extends across the interior of said machine side housing portion within said enclosed housing, wherein said hydrophobic membrane and said electrostatic filter element are retained differently with the housing, said hydrophobic membrane being bonded first around its periphery to the pinch ring of said patient side housing portion by an adhesive interface and extending across the interior of said patient side housing portion within said enclosed housing, and said electrostatic filter element being retained subsequently mechanically in place adjacent said hydrophobic membrane within said enclosed housing solely by clamping between the opposing pinch rings of said housing, so that the patient side portion of said housing is isolated from said machine side portion by said hydrophobic membrane during assembly of said electrostatic filter element.

4. The filter of claim 3, further including scrim disposed adjacent said electrostatic filter element, said electrostatic filter element comprising an electrostatically charged mass of polypropylene fibers disposed between said scrim and said hydrophobic membrane.

5. The filter of claim 4 wherein said hydrophobic membrane comprises non-woven polypropylene media.

6. The filter of claim 5 wherein said scrim comprises a non-woven web of polypropylene fibers.

7. The filter of claim 6 wherein said scrim is bonded to said electrostatic filter element.

8. The filter of claim 3 wherein said housing portions are fabricated of injection molded plastic material.

9. The filter of claim 8 wherein said plastic material is styrene-butadiene resin.

10. A method of fabricating a hydrophobic electrostatic breathing filter utilizing a patient side filter housing portion and a machine side filter housing portion each of which includes an annular outer edge and an annular pinch ring arranged inside of said outer edge, said method comprising the steps of first applying an adhesive to the pinch ring of the patient side housing portion, positioning a hydrophobic membrane over the pinch ring of said patient side housing portion to effect a hermetic seal between said hydrophobic membrane and said pinch ring of said patient side housing portion utilizing an adhesive interface, subsequently positioning electrostatic filter material and scrim within said machine side housing portion adjacent the pinch ring of said machine side housing portion, placing the outer edges of said housing portions in opposed engaged relation to one another to position said pinch rings of said housing portions in at least partially opposed relation to one another, and sealing said engaged outer edges of said housing portions to one another to form an enclosed filter housing that includes said electrostatic filter material and scrim which are fixed in place solely by clamping between the opposed parts of said pinch rings adjacent to said hermetically sealed hydrophobic membrane, such that said hydrophobic membrane is retained with the housing in a different manner from that in which said electrostatic filter material is retained with the housing, and such that the patient side portion of said housing is isolated from said machine side portion by said hydrophobic membrane during assembly of said electrostatic filter material.

11. The method of claim 10 wherein said adhesive is a hot melt adhesive.

12. The method of claim 10 wherein said housing portions are fabricated of a plastic material, said step of sealing said outer edges of said housing portions to one another being effected by ultrasonic welding.

13. The method of claim 10 wherein said step of sealing said outer edges of said housing portions to one another is effected by use of a hot melt adhesive.

14. The method of claim 10 wherein said electrostatic filter material and scrim are so positioned within said machine side housing portion that said electrostatic filter material is disposed between said hydrophobic membrane and said scrim after said outer edges of said housing portions have been sealed to one another.

15. The method of claim 10 wherein said hydropo membrane, said electrostatic filter material, and said scrim each comprises of polypropylene material.

* * * * *